United States Patent [19]

Fukawa et al.

[11] Patent Number: 5,239,042
[45] Date of Patent: Aug. 24, 1993

[54] AMORPHOUS POLYMERS AND PROCESS FOR THE PRODUCTION THEREOF

[75] Inventors: Isaburo Fukawa, Kurashiki; Tsuneaki Tanabe, Nobeoka, both of Japan

[73] Assignee: Asahi Kasei Kogyo Kabushiki Kaisha, Osaka, Japan

[21] Appl. No.: 773,956

[22] PCT Filed: Mar. 16, 1990

[86] PCT No.: PCT/JP90/00351

§ 371 Date: Nov. 15, 1991

§ 102(e) Date: Nov. 15, 1991

[87] PCT Pub. No.: WO91/13929

PCT Pub. Date: Sep. 19, 1991

[51] Int. Cl.$^5$ .............................................. C08G 14/00
[52] U.S. Cl. ................................... 528/125; 528/126; 528/128; 528/171; 528/174; 528/219; 528/220; 528/223; 528/370; 528/371; 528/373; 528/402; 528/403; 528/405; 528/408; 528/417; 524/729; 524/730; 524/787; 524/789
[58] Field of Search ............... 528/125, 126, 128, 171, 528/174, 219, 220, 223, 370, 371, 373, 402, 403, 405, 408, 417; 524/729, 730, 787, 789

[56] References Cited

U.S. PATENT DOCUMENTS 3,441,538 4/1969 Marks ..................................... 528/26

FOREIGN PATENT DOCUMENTS

| | | |
|---|---|---|
| 59-30822 | 2/1984 | Japan . |
| 61-211336 | 9/1986 | Japan . |
| 63-152633 | 6/1988 | Japan . |
| 63-182341 | 7/1988 | Japan . |
| 64-74223 | 3/1989 | Japan . |
| 01-074223 | 3/1989 | Japan . |
| 02-272023 | 11/1990 | Japan . |

OTHER PUBLICATIONS

CA114(24):237776t.
CA111(20):174914b.

*Primary Examiner*—Samuel A. Acquah
*Attorney, Agent, or Firm*—Birch, Stewart, Kolasch & Birch

[57] ABSTRACT

There are disclosed dibenzofuran amorphous polymer comprising a recurring unit represented by following formula (II) and having a molecular weight giving a reduced viscosity of at least 0.2 dl/g as measured in the form of a 0.5% (W/V) solution in N-methyl-pyrrolidone at 25° C., a process for producing said amorphous polymer, a dibenzofuran copolymer comprising, in addition to a recurring unit represented by following formula (II), at least one type of recurring unit represented by following general formula (III) in a specific proportion and having a molecular weight giving a reduced viscosity of at least 0.2 dl/g as measured in the form of a 0.5% (W/V) solution in concentrated sulfuric acid at 25° C., and a process for producing said copolymer.

Formula: (II)

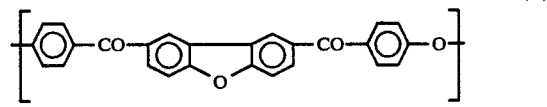

General Formula (III): (III)

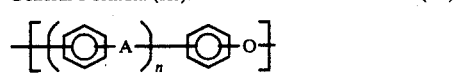

wherein A is —O—, —CO—, —S—, —SO$_2$—, a divalent alkylene group or a single bond and n is a number of 0, 1 or 2. There are also disclosed benzofuran derivatives useful as a starting material and a process for producing said derivatives. The above-mentioned amorphous polymer and copolymer are excellent in stability at the time of molding, low in polarity an low in moisture absorption, so that they are useful as starting materials for the manufacture of molded articles.

10 Claims, 3 Drawing Sheets

AMORPHOUS POLYMERS AND PROCESS FOR THE PRODUCTION THEREOF

TECHNICAL FIELD OF THE INVENTION

The present invention relates to a novel dibenzofuran amorphous polymer (hereinafter simply referred to as amorphous polymer), a dibenzofuran copolymer (hereinafter simply referred to as copolymer) and a process for the production thereof. More particularly, the present invention relates to an amorphous polymer having a high glass transition temperature, an excellent heat stability, a smaller polarity as compared with prior amorphous polymers and an excellent heat resistance, a copolymer having the same properties as above, and a process for affectively producing these polymers.

BACKGROUND ART

As typical examples of the prior heat resistant amorphous resin, aromatic polyether-sulfone (for example, Victrex PES ®, manufactured by ICI), polyether-imide (for example, Ultem ®, manufactured by GE) and the like are known. Although these resins are excellent heat-resistant engineering resins having a high glass transition point and usable at high temperatures, since they have highly polar groups such as sulfone group or imide group in their molecule, their performance is greatly affected by moisture absorption. In addition, these resins have a high dielectric constant. Thus, their use in the electrical industry is inevitably restricted. Further, since the sulfone group and imide group are poor in heat stability, these polymers are insufficient in stability when molded at high temperatures, and can undergo foaming, decomposition, coloration, etc., during the molding operation.

On the other hand, as resins having better heat stability, various aromatic polyether-ketones comprising only aromatic rings, ketone groups and ether groups are known. For example, there are known Victrex PEER ® manufactured by ICI, polymers represented by general formula (I):

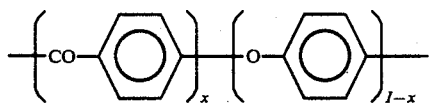

wherein the value of x varies, polymers prepared by introducing biphenylene structure or naphthalene structure thereinto, and the like. However, all of these resins are made of a crystalline polymer, and any amorphous totally aromatic polyether-ketone is not yet known. Although these crystalline resins are excellent in heat resistance as mentioned above, they are insufficient in dimensional stability and inferior in high-temperature stiffness due to their low glass transition temperature.

Aside from the above, polymers having a dibenzofuran skeleton prepared by allowing dibenzofuran to react with tere(iso)phthalic acid chloride in the following manner have also been reported. However, the polymers obtained by this method are all low in molecular weight, or fragile and colored.

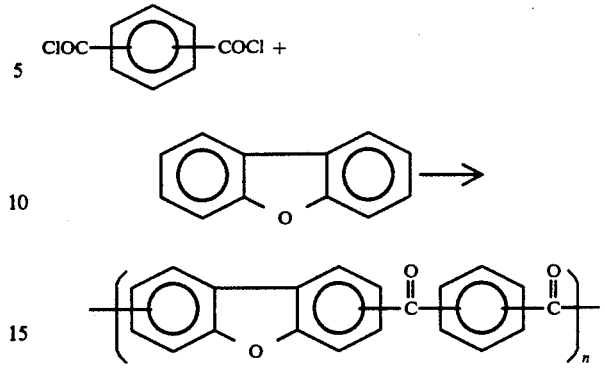

That is, there is disclosed a trimer in J. Appl. Polym. Sci. 9, (5) 1955 (165). There is disclosed a low molecular weight polymer of which reduced viscosity was 0.18 dl/g in U.S. Pat. No. 3,441,538. And there is disclosed a deep red-colored brittle film in Example 3 (Comparative Example) of Japanese Patent Unexamined Publication Kokai (Laid-Open) No. 63-399231.

In Japanese Patent Unexamined Publication Kokai (Laid-Open) No. 63-399231, this was deduced to be attributed to the fact that by the Friedel-Crafts method, an acrylation was not restricted the para position but it took place also in the ortho position, which activated the oxygen group, thereby caused branching and coloration.

As mentioned above, any dibenzofuran skeleton-containing polymer having a high molecular weight and a high stiffness has not been obtained.

In Japanese Patent Unexamined Publication Kokai (laid-Open) No. 61-211336, a production of a polymer by Friedel-Crafts reaction was described, where dibenzofuran was referred to as one of the 15 monomers used as nucleophilic copolymerizable components, and oxybis(4,4'-benzoyl chloride) was referred to as one of the 27 monomers used as electrophilic copolymerizable components. However, there is nothing disclosed in the specification as to a reaction of the two monomers in combination and the polymer formed by the reaction.

DISCLOSURE OF THE INVENTION

Under the above circumstances, the object of the present invention is to provide a heat resistant dibenzofuran amorphous polymer and dibenzofuran copolymer, which can be used at high temperatures and are excellent in stability at the time of molding, low in polarity and low in moisture absorption.

With the object of developing heat-resistant amorphous polymer and copolymer having the above-mentioned desirable properties, the present inventors have conducted extensive studies to find: that by partially introducing a dibenzofuran structure into the ether linkages of an aromatic polyether-ketone, the aromatic polyether-ketone can be made amorphous; and that a novel copolymer having a high glass transition temperature can be obtained. Based on this finding, the present invention has been accomplished.

Thus, according to the first aspect of the present invention, there is provided an amorphous polymer comprising recurring units represented by formula (II):

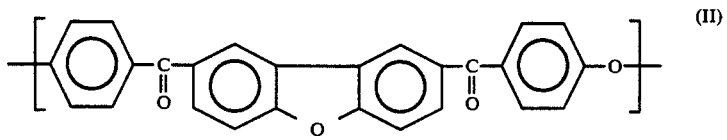

which has such a molecular weight that its reduced viscosity at a concentration of 0.5% (W/V) in N-methylpyrrolidone at 25° C. is 0.2 dl/g or greater.

According to the present invention, the above-mentioned amorphous polymer can be produced either by allowing 2,8-bis(4-halogenobenzoyl)-dibenzofuran to react with a carbonate or hydrogen carbonate of an alkali metal in the presence of a silica compound catalyst, or by carrying out a polycondensation reaction between 2,8-bis(4-halogenobenzoyl)-dibenzofuran and 2,8-bis(4-hydroxybenzoyl)-dibenzofuran in the presence of an alkali.

According to the second aspect of the present invention, there is provided a dibenzofuran type copolymer in which the molecular structure thereof comprises at least one constitutional unit selected from the group consisting of constitutional unit (a) represented by formula (II):

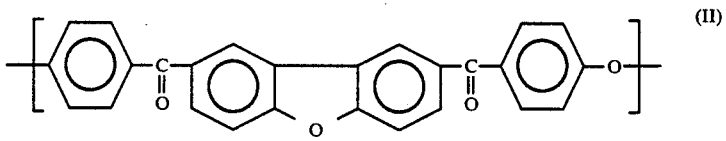

and constitutional unit (b) represented by general formula (III):

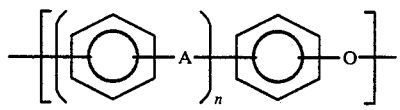

wherein A is —O—, —CO—, —S—, —SO₂—, a divalent alkylene group or a single bond and n is a number of 0, 1 or 2, wherein the molar ratio of constitutional unit (a) to constitutional unit (b) in the molecule is in the range of 10:90 to 99:1 and the copolymer has a molecular weight giving a reduced viscosity of 0.2 dl/g or greater when measured in the form of a 0.5% (W/V) solution in concentrated sulfuric acid at 25° C.

BEST MODE FOR THE PRACTICE OF THE INVENTION

Figure 1:
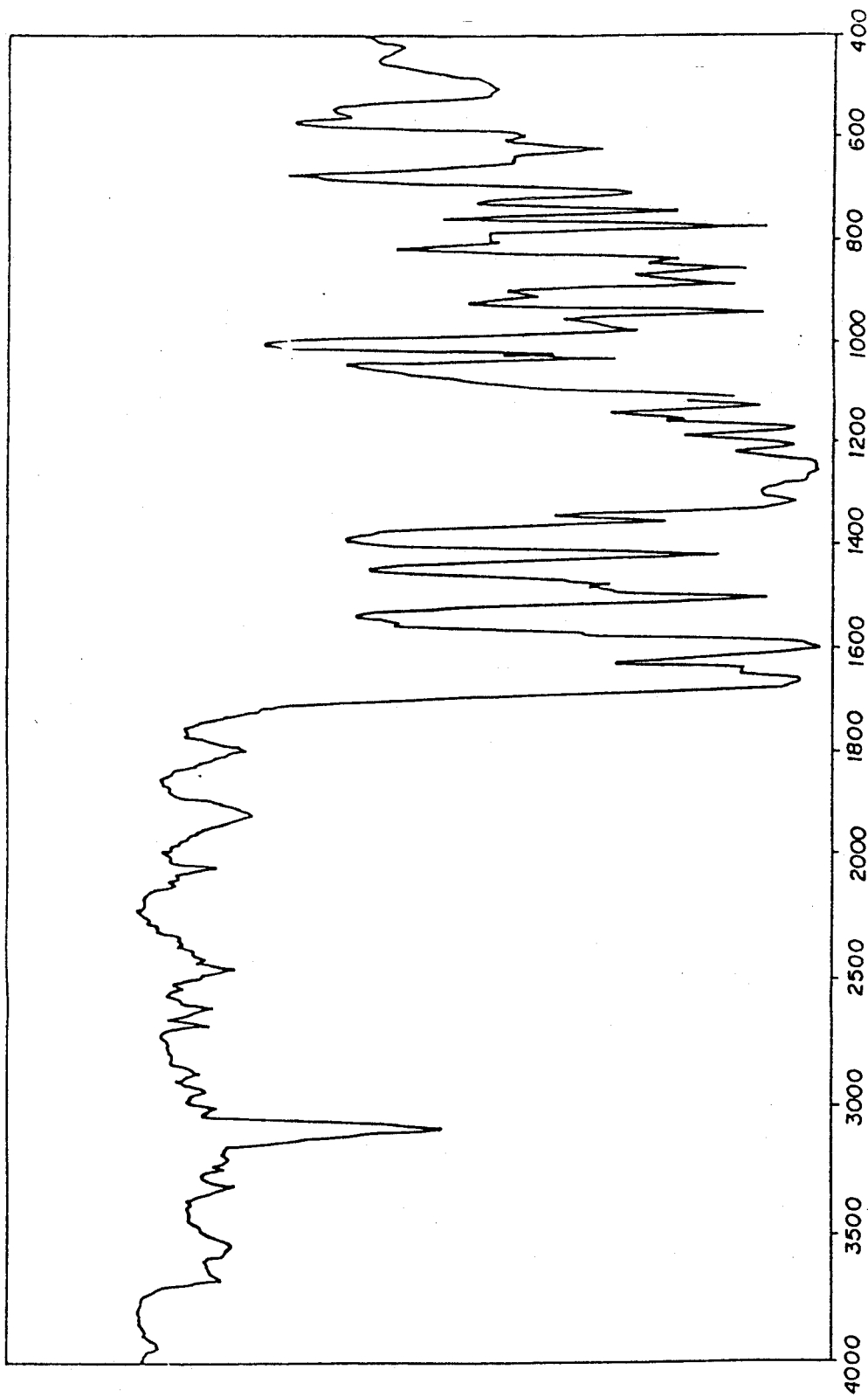
FIG. 1 to FIG. 3 are each respectively an infrared absorption spectral chart of an amorphous polymer, a wide angle X ray diffraction chart of one copolymer and an infrared absorption spectral chart of the copolymer, according to the present invention.

Hereinunder, the present invention will be illustrated in greater detail.

(1) Illustration Of Amorphous Polymer

The amorphous polymer of the present invention is an aromatic polyether-ketone in which the recurring unit thereof has a dibenzofuran structure as shown in above-mentioned formula (II).

The dibenzofuran structure can sometimes contain a dibenzofuran isomer structure which originated from a starting compound. Amorphous polymers having such a dibenzofuran structure containing a dibenzofuran isomer structure are also included in the scope of the present invention.

As examples of said dibenzofuran isomer structure, the following can be referred to:

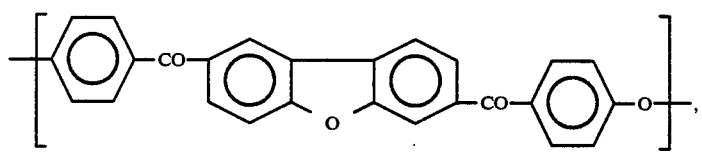

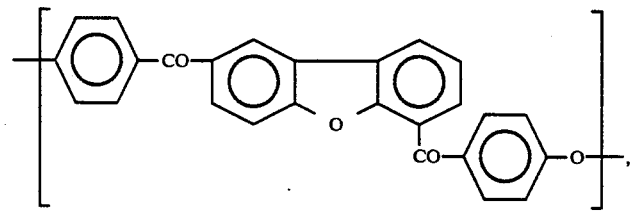

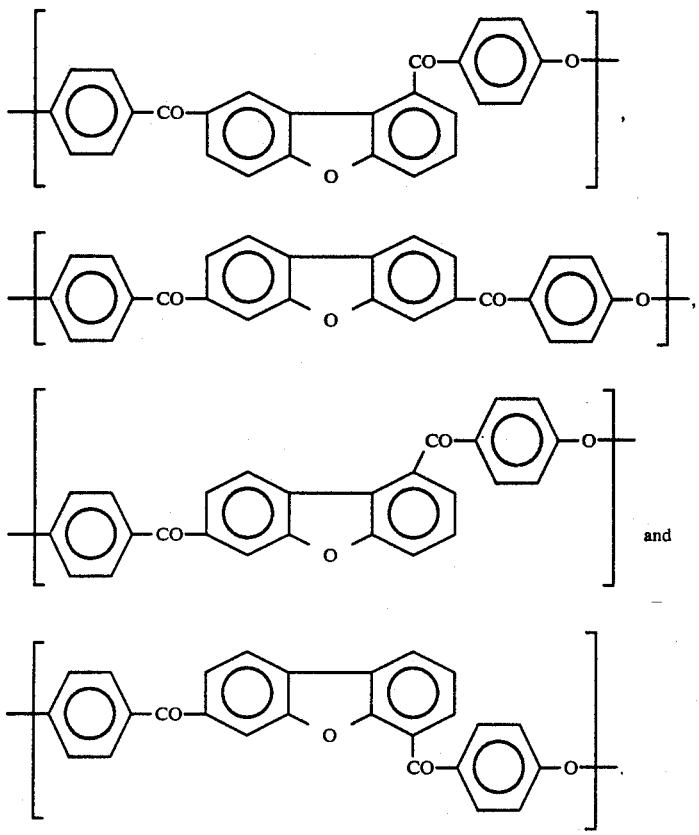

, and

.

Usually, the structure represented by formula (II) occupies at least 70% by mole of the total dibenzofuran structure.

According to the first method of the present invention, the amorphous polymer can be produced by an ether-forming self condensation of 2,8-bis(4-halogenobenzoyl)-dibenzofuran using a carbonate or hydrogen carbonate of an alkali metal in the presence of a silica compound catalyst. This reaction can be represented, for example, by the following reaction scheme:

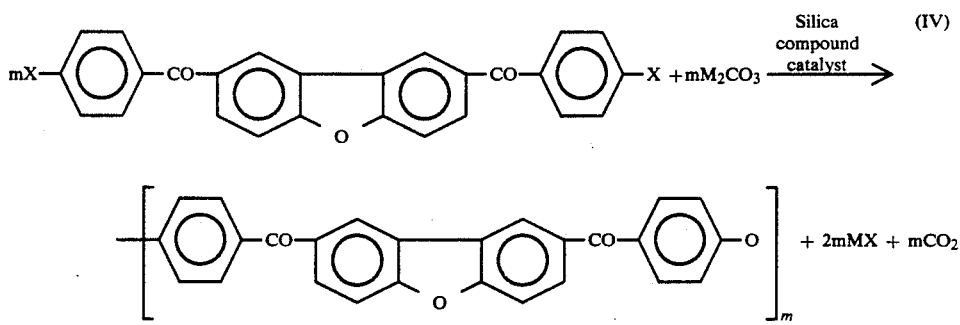

wherein X is a halogen atom and M is an alkali metal.

In this reaction, the reaction proceeds more rapidly when the halogen atom of the starting 2,8-bis(4-halogenobenzoyl)-dibenzofuran is a fluorine atom rather than when the halogen atom is a chlorine atom. Since fluorine compounds are generally more expensive than chlorine compounds, the use of 2,8-bis(4-chlorobenzoyl)-dibenzofuran in the presence of a small quantity of a copper salt as a co-catalyst for accelerating the reaction is also advantageous.

The 2,8-bis(4-halogenobenzoyl)-dibenzofuran may contain isomers such as:

2,7-bis(4-halogenobenzoyl)-dibenzofuran,
2,6-bis(4-halogenobenzoyl)-dibenzofuran,
2,9-bis(4-halogenobenzoyl)-dibenzofuran,
3,7-bis(4-halogenobenzoyl)-dibenzofuran,
3,9-bis(4-halogenobenzoyl)-dibenzofuran,
3,6-bis(4-halogenobenzoyl)-dibenzofuran and the like.

Usually, the quantity of the isomer is smaller than 30% by mole.

Examples of the carbonate or hydrogen carbonate of alkali metal used in this reaction include potassium carbonate, sodium carbonate, cesium carbonate, potassium hydrogen carbonate, sodium hydrogen carbonate, sodium potassium carbonate and the like. These alkali metal salts may be used singly or in combination of at least two types thereof. If potassium salts and sodium salts are compared with each other, potassium salts are generally characterized in that they make the reaction proceed more rapidly, while sodium salts are characterized by a smaller extent of side reaction. Mixtures of a potassium salt and a sodium salt are also used preferably.

When these alkali metal salts are used after pulverization into fine powder, the reaction proceeds more rapidly. In order to obtain a high polymer, the alkali metal salt must be used in an amount of at least 2 gram-atoms (one mole in the case of carbonate, and 2 moles in the case of hydrogen carbonate) as expressed in terms of alkali metal per one mole of the monomer. Although the velocity of the reaction can be increased by using an excessive quantity of alkali metal salt, the use of too large a quantity of the alkali metal salt is disadvantageous from the viewpoint of production, cost; and sometimes it can induce undesirable side reactions. Accordingly, a preferable quantity of the alkali metal salt is selected from the range of 1-4 moles in the case of carbonate and 2-8 moles in the case of hydrogen carbonate. And a particularly preferable quantity of the alkali metal salt is selected from the range of 1-1.5 moles in the case in which the salt is a carbonate and 2-3 moles in the case of hydrogen carbonate, per mole of the starting monomer.

As compared with alkali metal carbonates, alkali metal hydrogen carbonates are characterized in that they are higher in terms of reaction velocity, although they must be used in a larger quantity than alkali metal carbonates and they form water during the reaction which must be removed from the system.

In this reaction, it is necessary to use a silica compound catalyst. Silica type catalysts, such as dry process silica, wet process silica, silica gel and the like, and silica-alumina type catalysts, can be the silica compound catalyst used. As said silica-alumina type catalyst, silica-alumina compounds of various compositions, zeolite, active clay, sepiolite, montmorillonite, diatomaceous earth and the like can be referred to.

These catalysts are preferably used in the form of finely pulverized powder in order to increase the reaction velocity. Although the amount of catalyst is not critical, it is usually selected from a range of 0.1-100% by weight and preferably 1-30% by weight, based on the starting monomer. If the amount of catalyst is smaller than 0.1% by weight, the effect of the added catalyst cannot be exhibited sufficiently. If it exceeds 100% by weight, the reaction velocity cannot be enhanced to any significant extent resulting from this increase in the amount of the catalyst, but sometimes this even increases the viscosity of reaction system thereby causing an undesirable result.

This reaction can be accelerated by adding a co-catalyst such as copper, copper compound or alkali metal fluoride. The effect brought about by these co-catalysts is particularly remarkably exhibited when a chlorine compound is used as a relatively slow reacting monomer or when a sodium salt is used as the alkali metal salt. A combination of two types of co-catalysts, namely a copper or copper compound co-catalyst and an alkali metal fluoride co-catalyst, is also usable. As the copper or copper compound used as the co-catalyst, metallic copper and a variety of monovalent and divalent copper compounds can be referred to. Among those which are particularly preferable are various cuprous halides (cuprous chloride, cuprous bromide, cuprous iodide and the like), cupric halides (cupric chloride, cupric bromide and the like), cuprous oxide, cupric oxide, copper hydroxides, copper sulfates, copper basic carbonates, copper acetylacetonates, copper acetates, copper sulfides and the like. These may be used in the form of a mixture, and may be used either in an anhydrous form or in a state in which they contain crystalline water. As the alkali metal fluoride, potassium fluoride and cesium fluoride are preferable. Although the amount of the co-catalyst used is not critical, an amount of 0.1-10% by weight based on the weight of the catalyst is preferable.

The co-catalyst may be merely added to the reaction system together with a catalyst. In the case of copper salts, the co-catalyst may be previously supported on the catalyst surface. It is also possible to replace the alkali metal ion of zeolite with copper ion.

Although this reaction can be carried out in the absence of a solvent, it may also be carried out in an appropriate solvent. In the general production of aromatic polyether-ketones by polycondensation, the formed aromatic polyether-ketone is crystalline and unlikely to be dissolved in solvent, so that the reaction must be carried out at high temperatures of 300° C. or above. Accordingly, special solvents stable at high temperatures, such as aromatic sulfones, aromatic ketones and the like, must be used as the solvent. On the other hand, the amorphous polymer of the present invention is soluble in general solvents, and therefore, the polymerization of the present invention can be carried out at temperatures lower than 300° C., by using a more conventional solvent such as sulfolane and the like.

The solvent usable in this reaction is not critical. Arbitrarily selected solvents may be used as long as they are stable at the reaction temperature. Examples of these solvents include ketones such as acetophenone, benzophenone, isophthalophenone, xanthone, phenoxybenzophenone and the like; sulfones such as sulfolane, dimethyl sulfone, diphenyl sulfone and the like; sulfoxides such as dimethyl sulfoxide, diphenyl sulfoxide and the like; ethers such as diphenyl ether and the like. amides such as N-methylpyrrolidine, hexamethylphosphoric triamide and the like; hydrocarbons such as biphenyl, terphenyl, naphthalene, decaline and the like; and halogenated hydrocarbons such as chlorinated biphenyl, dichlorobenzene and the like. All of these solvents have a high boiling point and are usable in the reaction under normal pressures. When the reaction is carried out under an elevated pressure, solvents having a lower boiling point can also be used. There is a tendency that the polymerization reaction proceeds more readily in a solvent having a higher polarity.

Although the amount of the solvent is not critical, an amount of solvent giving a polymer concentration of 5-50 W/V % is recommended from the viewpoint of the balance between the efficiency of the reaction and the viscosity of the liquid reaction mixture.

Although the reaction temperature varies depending on the reaction conditions, such as types of halides, types of alkali metal salts, etc., it is usually selected from a range of 150° C. to 400° C. If the temperature is lower than 150° C., the reaction velocity is impractically low. If the temperature exceeds 400° C., undesirable side reactions are likely to take place. Stepwise elevation of reaction temperature is one of the preferable embodiments.

In order to realize a higher heat stability, the polymer solution thus formed may be subjected to a conventional molecular end stabilizing treatment using an active halide compound, such as methyl chloride, 4-fluorobenzophenone, 4,4'-difluorobenzophenone, 4-chlorobenzophenone and the like.

The polymer solution thus obtained is solidified by cooling and then pulverized, after which it is washed with an organic solvent, such as acetone, methanol or the like and water, or is once dissolved in a solvent and then precipitated in a non-solvent to obtain a purified polymer. When removal of silica is necessary, the polymer is dissolved in a solvent such as chloroform and then the solution is filtered or washed with an aqueous alkali solution. The copper compound used as a co-catalyst can be removed by treating it with an acid, alkali or solution of various copper chelating agents.

temperature is selected from a range of 150° C. to 400° C.

2,8-bis(4-fluorobenzoyl)-dibenzofuran and 2,8-bis(4-hydroxybenzoyl)-dibenzofuran used in the method of the present invention are novel compounds. 2,8-bis(4-fluorobenzoyl)-dibenzofuran can readily be produced by a Friedel-Crafts reaction of dibenzofuran and 4-fluorobenzoyl chloride. 2,8-bis(4-hydroxybenzoyl)-dibenzofuran can readily be produced by hydrolyzing the above-mentioned 2,8-bis(4-fluorobenzoyl)-dibenzofuran.

It is also possible to obtain the amorphous polymer of the present invention by carrying out a partial hydrolysis to obtain the following compound:

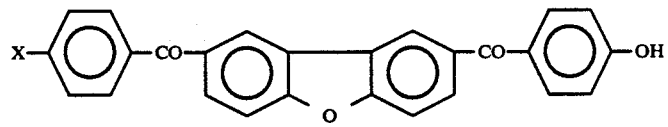

According to the second method of the present invention, 2,8-bis(4-halogenobenzoyl)-dibenzofuran and 2,8-bis(4-hydroxybenzoyl)-dibenzofuran are subjected to a polycondensation by nucleophilic substitution reaction in the presence of an alkali to form the intended amorphous polymer. This reaction is represented by the following reaction scheme:

and subjecting it to a self-condensation in the presence of an alkali.

The amorphous polymer of the present invention must have such a molecular weight so as to give a reduced viscosity of 0.2 dl/g or higher as measured in the form of a 0.5% (W/V) solution in N-methylpyrrolidone at 25° C. Polymers of which reduced viscosity is lower (V)

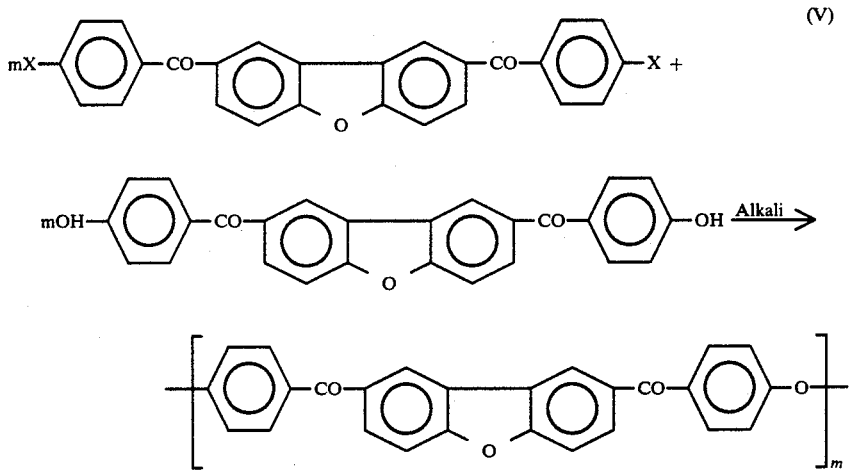

wherein X is a halogen atom.

As the alkali usable in this reaction, carbonates and hydrogen carbonates of alkali metals can be referred to. As these alkali metal salts, the same alkali metal salts as mentioned in the first method can be referred to. Usually, these alkali metal salts are used in an amount of 0.5–4 gram-atoms as expressed in terms of alkali metal, per mole of the starting 2,8-bis-(4-hydroxybenzoyl)-dibenzofuran. It is also allowable in the present invention to first convert the 2,8-bis-(4-hydroxybenzoyl)-dibenzofuran as one of the starting materials into an alkali metal salt.

The starting compounds, i.e., 2,8-bis-(4-halogenobenzoyl)-dibenzofuran and 2,8-bis(4-hydroxybenzoyl)-dibenzofuran are used in an approximate equimolar proportion. The reaction may be carried out either in the absence of solvent or in the presence of an appropriate solvent. As the solvent, the same ones as mentioned in the first method can be used. Usually, the reaction than 0.2 dl/g are inferior in mechanical properties, and their molded products are practically unusable.

(2) Illustration Of The Dibenzofuran Type Copolymer Of The Present Invention

Examples of the copolymer of the present invention include the following:

1. A copolymer comprising:

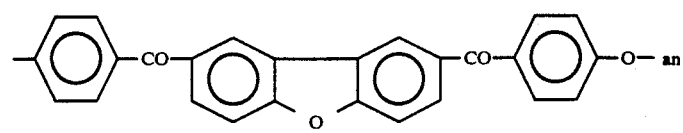

2. A copolymer comprising:
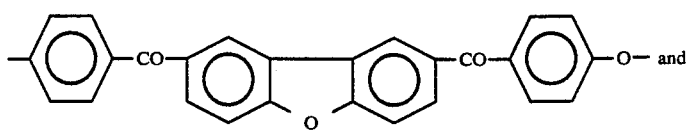
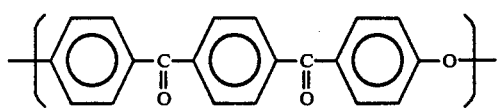
3. A copolymer comprising:
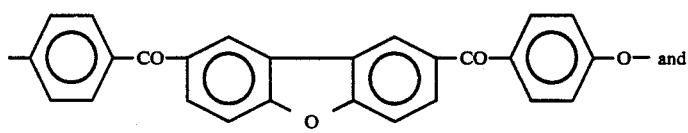
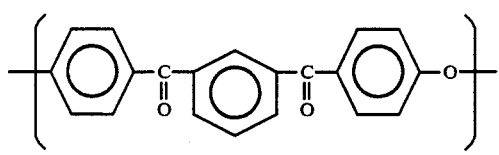
4. A copolymer comprising:
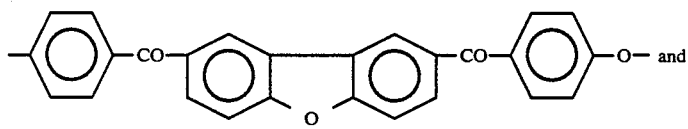
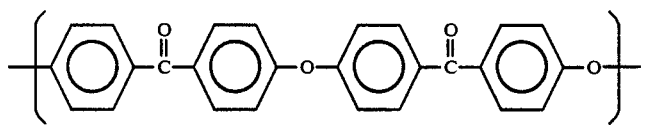
5. A copolymer comprising:
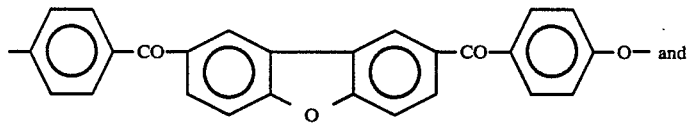
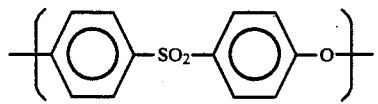
6. A copolymer comprising:
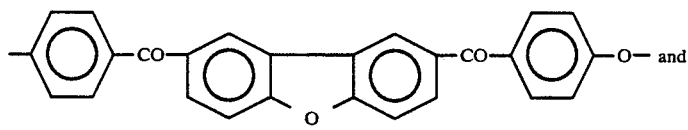

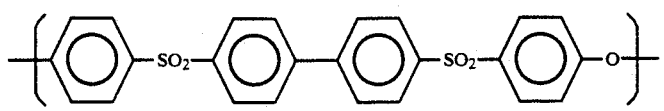
7. A copolymer comprising:
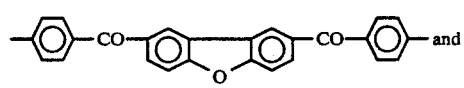
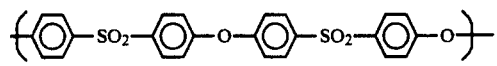
8. A polymer comprising:
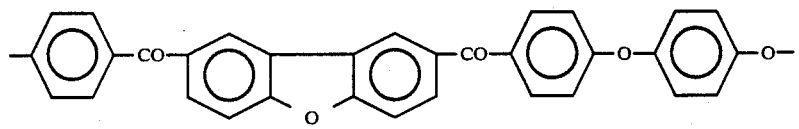
9. A polymer comprising:
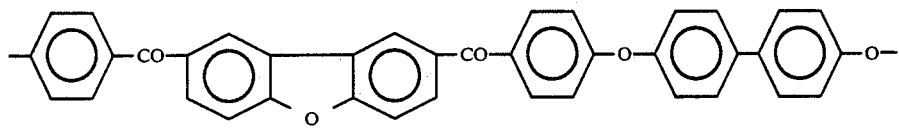
10. A polymer comprising:
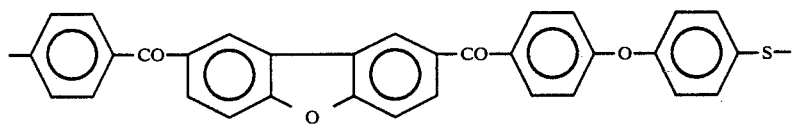
11. A polymer comprising:
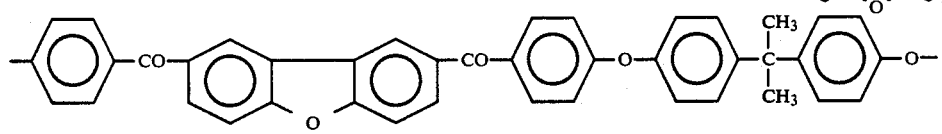
12. A polymer comprising:
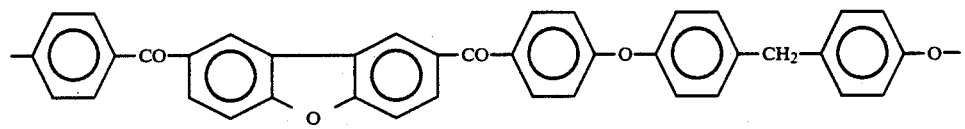
13. A polymer comprising:
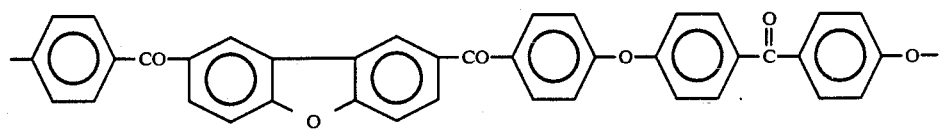
14. A polymer comprising:
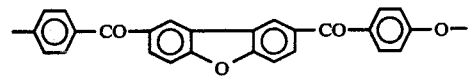
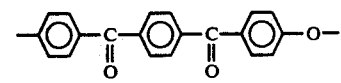
15. A polymer comprising:
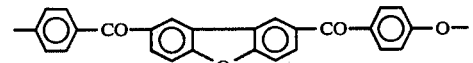

-continued

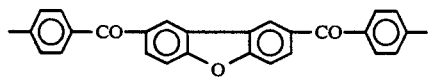

16. A polymer comprising:

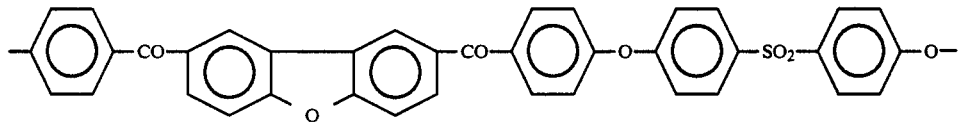

and the like.

Copolymers 1-7 mentioned above include both random copolymers and block copolymers.

Among these polymers, aromatic polyether-ketones having no sulfone group are preferable from the viewpoint of water absorption properties and heat resistance.

Further, as mentioned above, the structure:

constituting the above-mentioned copolymers may contain various isomeric structures up to an amount of 30% by mole.

Such polyether-ketone copolymers can be produced, for example, either by carrying out an ether-forming self-polycondensation of 2,8-bis(4-halogenobenzoyl)-dibenzofuran and an aromatic active dihalide by using a carbonate or hydrogen carbonate of an alkali metal in the presence of a silica type catalyst, or by carrying out a polycondensation reaction of an aromatic active dihalide and an aromatic dihydroxy compound in the presence of an alkali by using at least one member selected from the group consisting of 2,8-bis(4-halogenobenzoyl)-dibenzofuran and 2,8-bis(4-hydroxybenzoyl)-dibenzofuran as a reactive component.

The ether-forming self-polycondensation reaction of 2,8-bis(4-halogenobenzoyl)-dibenzofuran and aromatic active dihalide using a carbonate or hydrogen carbonate of alkali metal in the presence of a silica type catalyst proceeds according to the following reaction scheme:

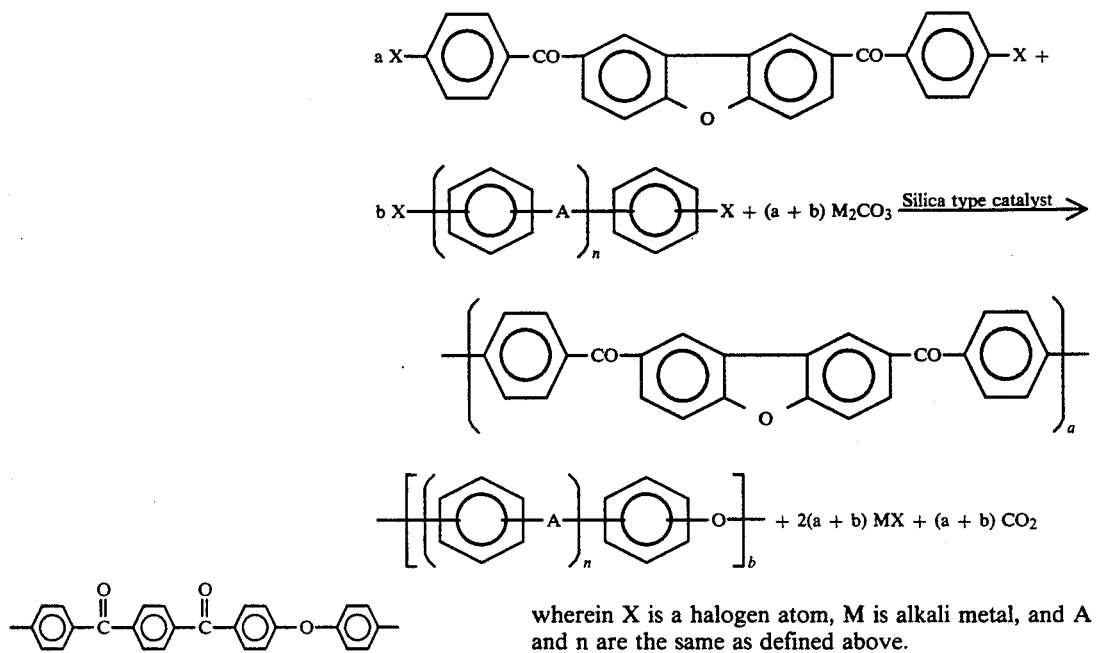

wherein X is a halogen atom, M is alkali metal, and A and n are the same as defined above.

In this reaction, it is necessary to select the molar ratio a:b of the two starting compounds from a range of 10:90 to 99:1.

If a mixture consisting of "a" moles of 2,8-bis(4-halogenobenzoyl)-dibenzofuran and "b" moles of aromatic active dihalide is polymerized, a random copolymer is obtained. If "a" moles of 2,8-bis-(4-halogenobenzoyl)-dibenzofuran is polymerized and thereafter "b" moles of aromatic active dihalide is added and polymerized, a block copolymer is obtained.

The ether oxygen atoms in the dibenzofuran type copolymers thus obtained, originated from the alkali metal carbonate.

Examples of the aromatic active dihalide used in the above-mentioned reaction include the following:
4,4'-difluorobenzophenone,
4,4'-dichlorobenzophenone,
4,4'-dibromobenzophenone,
4,4'-difluoroterephthalophenone,
4,4'-dichloroterephthalophenone,
4,4'-difluoroisophthalophenone,
4,4'-dichloroisophthalophenone,
4,4'-bis(4-fluorobenzoyl)-diphenyl ether,
4,4'-bis(4-chlorobenzoyl)-diphenyl ether,
4,4'-bis(4-fluorobenzoyl)-biphenyl,
4,4'-bis(4-chlorobenzoyl)-biphenyl,
4,4'-bis(4-fluorobenzoyl)-diphenyl sulfide,
4,4'-bis(4-chlorobenzoyl)-diphenyl sulfide,
4,4'-bis(4-fluorobenzoyl)-diphenylmethane,
4,4'-bis(4-chlorobenzoyl)-diphenylmethane, 4,4'-dichlorodiphenyl sulfone,
4,4'-bis(4-chlorobenzosulfonyl)-biphenyl, and the like.

If desired, the phenylene group in these compounds may be substituted with a substituent inert to the above-mentioned polycondensation reaction.

These aromatic active dihalides may be used singly or in combination of at least two types thereof.

As the halogen atom in these aromatic active dihalides and the 2,8-bis(4-halogenobenzoyl)-dibenzofuran to be reacted therewith, fluorine is most advantageous because it has a high reactivity and gives a high molecular weight in a short period of time. However, fluorine compounds are generally expensive. On the other hand, as compared with fluorine compounds, the corresponding chlorine compounds are lower in reaction velocity. However, their reaction can be accelerated by using a catalyst or a combination of catalyst and co-catalyst and, in addition, chlorine compounds are generally inexpensive. Accordingly, chlorine compounds are more advantageous industrially.

Preferable examples of the alkali metal carbonate and alkali metal hydrogen carbonate used in this reaction include potassium carbonate, sodium carbonate, cesium carbonate, potassium hydrogen carbonate, sodium hydrogen carbonate, sodium potassium carbonate and the like. They may be used singly or in combination of at least two types thereof. In a comparison between the potassium salts and sodium salts, the potassium salts are generally characterized with having a high reaction velocity, whereas the sodium salts are generally characterized with having side reactions, to a small extent. Mixtures of potassium salt and a sodium salt are also preferably usable.

Preferably, these alkali metal salts are used after pulverization into fine powder in order to increase reaction velocity. In order to obtain a high polymer, the alkali metal salt must be used in an amount of at least 2 gram-atoms (one mole in the case of carbonate and two moles in the case of hydrogen carbonate) as expressed in terms of alkali metal, per mole of the monomer. Although the reaction velocity can be increased by using the alkali metal salt in an excessive amount, the use of too large an amount of the alkali metal salt is disadvantageous from the viewpoint of production cost, and sometimes it might cause undesirable side reactions. Accordingly, the amount of alkali metal salt is preferably selected from a range of 1-4 moles in the case of a carbonate and 2-8 moles in the case of hydrogen carbonate, and particularly preferably from a range of 1-1.5 moles in the case of a carbonate and 2-3 moles in the case of hydrogen carbonate, all per mole of the starting monomer.

Alkali metal hydrogen carbonates must be used in a larger amount than that of alkali metal carbonates. And they form water during reaction, which must be removed. However, they are characterized by a high reaction velocity.

In this reaction, it is necessary to use a silica compound catalyst. Silica type catalysts, such as dry process silica, wet process silica, silica gel and the like and silica-alumina type catalysts, can be the silica compound catalyst used. As said silica-alumina type catalyst, silica-alumina compounds of various compositions, and mineral compounds such as zeolite, active clay, sepiolite, montmorillonite, diatomaceous earth and the like can be referred to.

These catalysts are preferably used in the form of finely pulverized powder in order to increase the reaction velocity. Although the amount of the catalyst is not critical, it is usually selected from a range of 0.1-100% by weight and preferably 1-30% by weight, based on the starting monomer. If the amount of catalyst is smaller than 0.1% by weight, the effect of the added catalyst cannot be exhibited sufficiently. If it exceeds 100% by weight, the reaction velocity cannot be enhanced to any significant extent resulting from this increase in the amount of the catalyst, but sometimes this even increases the viscosity of the reaction system thereby causing an undesirable result.

This reaction can be accelerated by adding a co-catalyst such as copper, copper compound or alkali metal fluoride. The effect brought about by these co-catalysts is particularly remarkably exhibited when a chlorine compound is used as a relatively slow reacting monomer or when a sodium salt is used as an alkali metal salt. A combination of two types of co-catalysts, namely a copper or copper compound co-catalyst and an alkali metal fluoride co-catalyst, is also usable. As the copper or copper compound used as the co-catalyst, metallic copper and a variety of monovalent and divalent copper compounds can be referred to. Among those which are preferable are various cuprous halides (cuprous chloride, cuprous bromide, cuprous iodide and the like), cupric halides (cupric chloride, cupric bromide and the like), cuprous oxide, cupric oxide, copper hydroxides, copper sulfates, copper basic carbonates, copper acetylacetonates, copper acetates, copper sulfides and the like. These may be used in the form of a mixture, and may be used either in an anhydrous form or in a state in which they contain crystalline water. As the alkali metal fluoride, potassium fluoride and cesium fluoride are preferable. Although the amount of the co-catalyst used is not critical, an amount of 0.1-10% by weight based on the weight of a catalyst is preferable.

The co-catalyst may be merely added to the reaction system together with a catalyst. In the case of copper salts, the co-catalyst may be previously supported on the catalyst surface. It is also possible to replace the alkali metal ion of zeolite with copper ion.

Although this reaction can be carried out in the absence of solvent, it may also be carried out in an appropriate solvent. In the general production of aromatic polyether-ketones by polycondensation, the formed aromatic polyether-ketone is crystalline and unlikely to be dissolved in solvent, so that the reaction must be carried out at high temperatures of 300° C. or above. Accordingly, special solvents stable at high temperatures, such as aromatic sulfones, aromatic ketones and the like, must be used as the solvent. On the other hand, the copolymer of the present invention is soluble in general solvents so far as the content of dibenzofuran unit is not lower than a specified value and the copolymer can be amorphous. Therefore, the polymerization of the present invention can be carried out at a temperature of at most 300° C., by using a more conventional solvent such as sulfolane and the like.

The solvent usable in this reaction is not critical, but arbitrarily selected solvents may be used as long as they are stable at the reaction temperature. Examples of these solvents include ketones such as acetophenone, benzophenone, isophthalophenone, xanthone, dimethyl sulfone, diphenyl sulfone and the like; sulfoxides such as dimethyl sulfoxide, diphenyl sulfoxide and the like; ethers such as diphenyl ether and the like; amides such as N-methylpyrrolidone, hexamethylphosphoric triamide and the like; hydrocarbons such as biphenyl, terphenyl, naphthalene, decaline and the like; and halogenated hydrocarbons such as chlorinated biphenyl, dichlorobenzene and the like. All of these solvents have a high boiling point and are usable in the reaction under normal pressures. When the reaction is carried out under an elevated pressure, solvents having a lower boiling point can also be used. There is a tendency that the polymerization reaction proceeds more readily in a solvent having a higher polarity.

Although the amount of the solvent is not critical, an amount of solvent giving a polymer concentration of 5-50% W/V is recommended from the viewpoint of the balance between the efficiency of the reaction and the viscosity of the liquid reaction mixture.

Although the reaction temperature varies depending on the reaction conditions, such as types of halides, types of alkali metal salts, etc., it is usually selected from a range of 150° C. to 400° C. If the temperature is lower than 150° C., the reaction velocity becomes impractically low. If the temperature exceeds 400° C., undesirable side reactions are likely to take place.

In order to realize a higher heat stability, the copolymer solution thus formed may be subjected to a conventional molecular end stabilizing treatment using an active halide compound such as methyl chloride, 4-fluorobenzophenone, 4,4'-difluorobenzophenone, 4-chlorobenzophenone and the like.

The copolymer solution thus obtained is solidified by cooling and then pulverized, after which it is washed with an organic solvent, such as acetone, methanol or the like and water, or is once dissolved in a solvent and then precipitated in a non-solvent to obtain a purified polymer. When removal of silica is necessary, the polymer is dissolved in a solvent such as chloroform and then the solution is filtered or washed with an aqueous alkali solution. The copper compound used as a co-catalyst can be removed by treating it with an acid, alkali or solution of various copper chelating agents.

Next, when the polyether-ketone copolymer of the present invention is produced by a nucleophilic substitution reaction using at least one member selected from the group consisting of 2,8-bis(4-halogenobenzoyl)-dibenzofuran and 2,8-bis(4-hydroxybenzoyl)-dibenzofuran as a component in the presence of an alkali, the reaction is carried out according to the following reaction scheme:

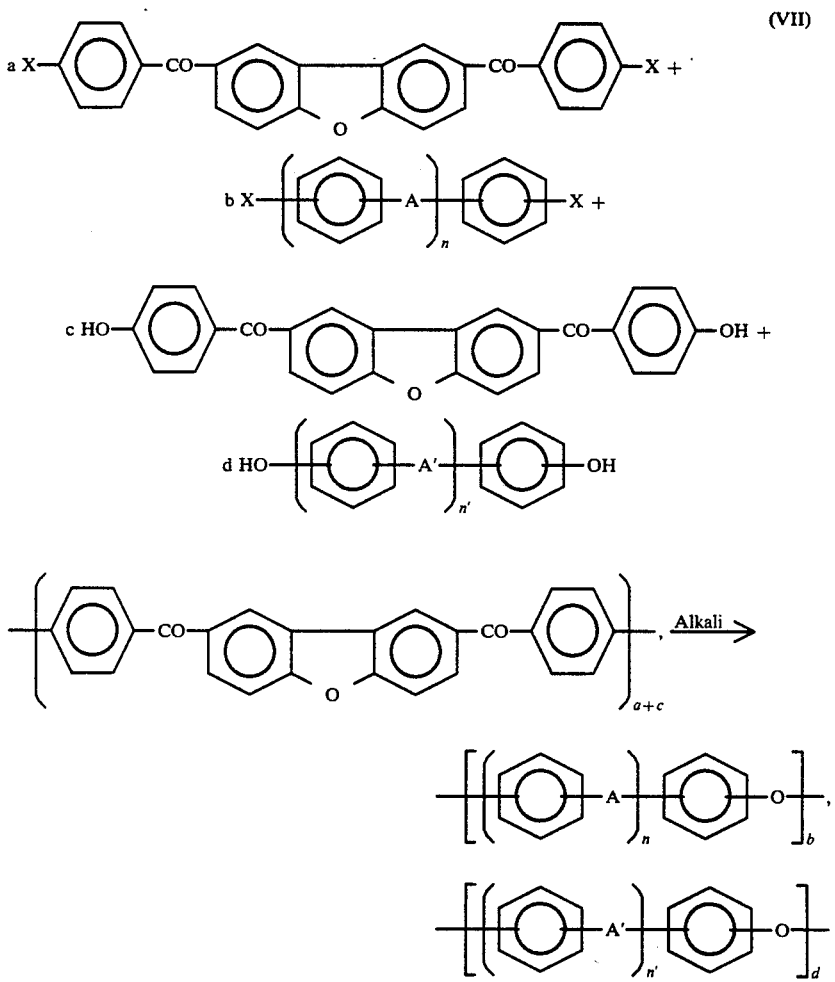

wherein X, A and n are the same as defined above and A' and n' have the same meaning as those of A and n defined above.

In the above-mentioned scheme, one or two types of monomer components of the four types of monomer components are not necessarily added. However, in order to obtain a copolymer of the present invention, the molar ratio (a+c)/(b+d) must be in the range of 0.1/0.9 to 0.99/0.01, wherein (a+c) is a total molar quantity of the monomers having a dibenzofuran structure and (b+d) is a total molar quantity of the other monomers.

Further, in order to obtain a copolymer having a high degree of polymerization, it is desirable that the molar ratio (a+b)/(c+d) be preferably in the range of 0.95/1.0 to 1.05/1.0 and particularly in the range of 1.0/1.0 to 1.03/1.0, wherein (a+b) is a total molar quantity of the halide monomers and (c+d) is a total molar quantity of the phenol monomers.

As the aromatic active dihalides used in this reaction, the same ones as those mentioned above can be referred to. As examples of the aromatic dihydroxy compound, the following can be referred to:
hydroquinone,
resorcin,
4,4'-biphenol,
4,4'-dihydroxydiphenyl ether,
4,4'-dihydroxydiphenyl sulfide,
4,4'-dihydroxybenzophenone,
2,2-bis(4-hydroxyphenyl)-propane,
1,1,1,1,3,3,3-hexafluoro-2,2-bis(4-hydroxyphenyl)propane,
4,4'-bis(4-hydroxybenzoyl)-diphenyl ether,
naphthalenediol, and the like. Further, 2-(4-chlorobenzoyl)-8-(4-hydroxybenzoyl)-dibenzofuran and 4-chloro-4'-hydroxybenzophenone are also usable as a partial component.

As the alkali used in this reaction, carbonates and hydrogen carbonates of alkali metals can be referred to.

As the alkali metal salts, the same ones as mentioned in the above method can be used. These alkali metal salts are used in an amount of 0.5–4 gram-atoms as expressed in terms of alkali metal per mole of the total phenolic monomers.

In this method, it is also possible to use the phenolic monomer previously converted to an alkali metal salt.

This reaction may be carried out in the absence of any solvent or in the presence of an appropriate solvent. As the solvent, the same solvents as mentioned in the above mentioned can be used. The reaction temperature is usually selected from a range of 150° C. to 400° C.

Molecular end stabilization and purification of the polymer can also be performed in the same manner as mentioned in the above method.

The 2,8-bis(4-halogenobenzoyl)-dibenzofuran used in the production of the copolymer of the present invention can readily be produced by a Friedel-Crafts reaction of dibenzofuran and 4-halogenobenzoyl chloride. Although the Friedel-Crafts reaction yields a small quantity of isomers, they can be removed through recrystallization. If the quantity of the isomers is not greater than 30%, the product containing such isomers may be used in the subsequent reaction as is. Examples of the isomers include the following:

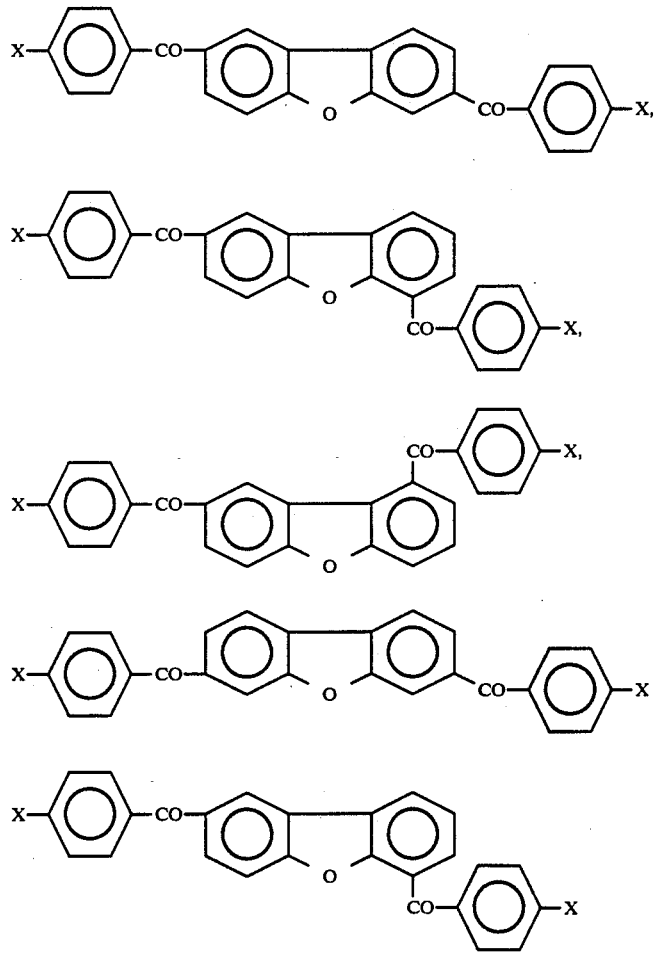

and the like.

The 2,8-bis(4-hydroxybenzoyl)-dibenzofuran used in the production of the copolymer of the present invention can readily be produced by hydrolyzing the above-mentioned 2,8-bis(4-fluorobenzoyl)-dibenzofuran.

In the copolymer of the present invention, the constitutional unit (a) is represented by the above-mentioned formula (II), and it can sometimes be comprised of isomeric dibenzofuran structures which originated from the starting compound. Even if the copolymer is a copolymer which contains isomeric structures, it can still be used in the present invention without any problems, as long as the content of the isomeric structures is not higher than 30% by mole. As examples of said isomeric structures of the constitutional unit (a), the following can be referred to:

value, it becomes amorphous. The composition range in which the polymer is amorphous varies depending on the type of polymer. For example, in the case of a copolymer represented by the following formula:

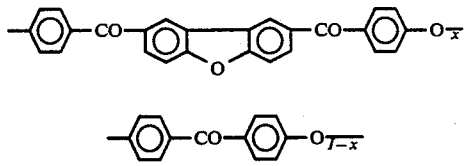

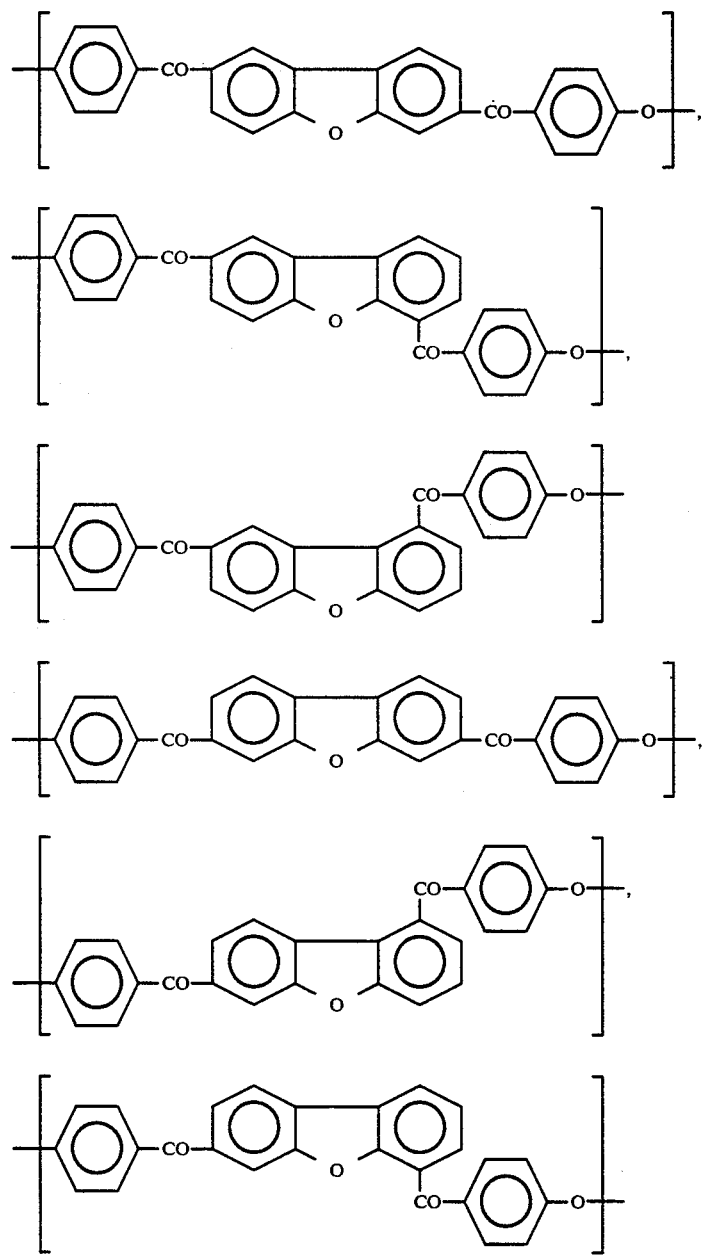

When the content of dibenzofuran units is low, the copolymer having the dibenzofuran structure of the present invention is crystalline similarly to the aromatic polyether-ketones reported so far. However, when the content of the dibenzofuran units exceeds a specified the copolymer is amorphous in a range of $x > 0.2$, roughly speaking.

There have hitherto been disclosed a variety of aromatic polyether-ketones, such as those represented by the following general formula:

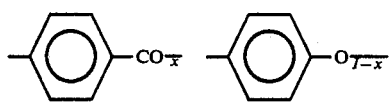

wherein x is varied, those obtained by introducing biphenyl structure or naphthalene structure into the above-mentioned general formula and the like. However, all of these known polyether-ketones are crystalline; and any amorphous totally aromatic polyether-ketone has never been disclosed until the present time.

Accordingly, it is an entirely unexpected fact that an amorphous polymer can be obtained by partially converting the linkages of an aromatic polyether-ketone to a dibenzofuran structure according to the present invention.

Further, although reaction products formed between dibenzofuran and tere(or iso)phthalic acid chloride are known, their structures are different from those of the polymer of the present invention.

The copolymer of the present invention must have a molecular weight corresponding to a reduced viscosity of at least 0.2 dl/g as measured in the form of a 0.5% (W/V) solution in a concentrated sulfuric acid at 25° C. If the reduced viscosity is lower than 0.2 dl/g, the copolymer is inferior in mechanical properties, and its molded product is practically unusable.

The copolymer of the present invention has a high glass transition temperature and is suitable for use in the formulation of various molded articles or films which are usable at high temperatures. Further, since it has a high heat stability, a high molding temperature can be adopted, so that an excellent moldability can be exhibited. Further, as compared with the prior heat-resistant amorphous resins, the copolymer of the present invention is lower in polarity and moisture absorption, so that it is characterized by having only a small change in properties upon exposure to moisture. Thus, the copolymer of the present invention is preferably usable in fields requiring the above-mentioned characteristic properties.

Further, among the polymers of the present invention, the amorphous copolymer is an absolutely excellent heat resistant resin, because it has excellent heat stability and low polarity which originated from the polyether-ketone structure, besides having excellent dimensional stability and transparency.

The polymers of the present invention can be used in any desired shape, for example, as an injection molded article, extruded article, coating, film, fiber and the like. Further, they can be used as an alloy or a composite by blending with various heat-resistant engineering plastics (polyether-ketones, sulfones, polyether-imides, aromatic polyesters, PPS), general-purpose engineering plastics, glass fiber, aramide fiber, carbon fiber, inorganic materials and the like.

EXAMPLES

Subsequently, the present invention is illustrated in more detail by way of the following examples. The present invention is by no means limited by these examples.

PRODUCTION EXAMPLE 1

Production of 2,8-bis(4-fluorobenzoyl)-dibenzofuran

Into a four-necked flask having a capacity of one liter, are charged 63.6 g (0.378 mole) of dibenzofuran, 126 g (0.946 mole) of aluminum chloride and 500 ml of o-dichlorobenzene. While cooling the mixture in a water bath and stirring it in an atmosphere of nitrogen, 150 g (0.95 mole) of p-fluorobenzoyl chloride is dropped thereinto over a period of about 30 minutes. Then, the reaction temperature is elevated up to 100° C. and kept at that temperature for 2 hours. After cooling, the reaction mixture is poured into a large quantity of 95% methanol, and the resulting precipitate is washed with water and methanol and recrystallized from toluene to obtain 114 g (yield 73%) of the intended product. NMR analysis revealed that the product contained about 10% of isomers.

By the same procedure as above, the corresponding chloro derivative [2,8-bis(4-chlorobenzoyl)dibenzofuran] is obtained.

PRODUCTION EXAMPLE 2

Production of 2,8-bis(4-hydroxybenzoyl)-dibenzofuran

Into an autoclave having a capacity of one liter, are charged 36 g (87 mmoles) of 2,8-bis(4-fluorobenzoyl)-dibenzofuran produced in Production Example 1, 8 g (450 mmoles) of sodium hydroxide, 360 ml of dimethyl sulfoxide and 180 ml of water. After replacing the inner atmosphere with nitrogen, the mixture is heated up to 130° C. over one hour and reacted at that temperature for 9 hours with stirring. The reaction mixture is cooled and neutralized with hydrochloric acid, and the resulting white precipitate is washed with water, dried and recrystallized from ethanol to obtain 20 g of 2,8-bis(4-hydroxybenzoyl)-dibenzofuran.

EXAMPLE 1

Into a 200 ml flask were charged 20.6 g (0.05 mole) of 2,8-bis(4-fluorobenzoyl)-dibenzofuran obtained in Production Example 1, 11 g (0.08 mole) of potassium carbonate, 2.0 g of silica (aerosil 300, manufactured by Nippon Aerosil Co.) and 30 g of diphenyl sulfone. After replacing the inner atmosphere with nitrogen, the temperature is elevated from room temperature to 300° C. over 30 minutes, and then the mixture is reacted at that temperature for 3 hours. After cooling, the reaction product is pulverized and repeatedly washed with water and acetone to obtain 19.3 g of a light yellow-violet powdery product. This product is soluble in chloroform, N-methylpyrrolidone and concentrated sulfuric acid. Its reduced viscosity is 0.74 dl/g as measured in the form of a 0.5% (W/V) solution in N-methylpyrrolidone at 25° C.

Its saturated water absorption is 0.21%. For comparison, saturated water absorptions of Victrex® PES 4100G (manufactured by ICI) and Ultem® 1000 (manufactured by GE) are also measured. The results are 0.43% and 0.25%, respectively.

Wide angle X ray diffraction analysis revealed that this polymer is amorphous. Its glass transition point is 230° C. FIG. 1 illustrates infrared absorption spectrum of this polymer.

EXAMPLE 2

The reaction of Example 1 is repeated except that the 2,8-bis(4-fluorobenzoyl)-dibenzofuran used in Example 1 is replaced with 22.3 g (0.05 mole) of 2,8-bis(4-chlorobenzoyl)-dibenzofuran obtained in Production Example 1; that 30 mg of cupric chloride is newly added; and that the reaction time is altered to 6 hours. As a result, a light yellow-violet powdery product is obtained. This polymer is amorphous, and its reduced viscosity at 25° C. and its glass transition point are almost same as those of the product of Example 1.

EXAMPLE 3

Into a flask having a capacity of 200 ml are charged 20.6 g (0.05 mole) of 2,8-bis(4-fluorobenzoyl)dibenzofuran obtained in Production Example 1, 20.4 g (0.05 mole) of 2,8-bis(4-hydroxybenzoyl)-dibenzofuran obtained in Production Example 2, 6.9 g (0.05 mole) of potassium carbonate and 40 g of diphenyl sulfone. By repeating the procedure of Example 1, a light yellow-violet powdery product is obtained.

This polymer is amorphous, and its reduced viscosity at 25° C. and glass transition temperature are almost same as those of the product of Example 1.

EXAMPLE 4

Into a flask having a capacity of 200 ml are charged 8.24 g (0.02 mole) of 2,8-bis(4-fluorobenzoyl)-dibenzofuran obtained in Production Example 1, 4.36 g (0.02 mole) of 4,4'-difluorobenzophenone, 9.66 g (0.07 mole) of potassium carbonate, 1.0 g of silica (Aerosil 300, manufactured by Nippon Aerosil Co.) and 25 g of benzophenone. After substituting the inner atmosphere with nitrogen, the mixture is heated from room temperature to 280° C. over about 30 minutes with stirring, and reacted at that temperature for 4 hours. The reaction mixture became a yellow viscous liquid. After cooling, it is pulverized, repeatedly washed with acetone and water, dissolved into chloroform, filtered and precipitated in a large quantity of methanol to obtain 11.3 g of a polymer as a white-colored powdery product.

Figure 2:
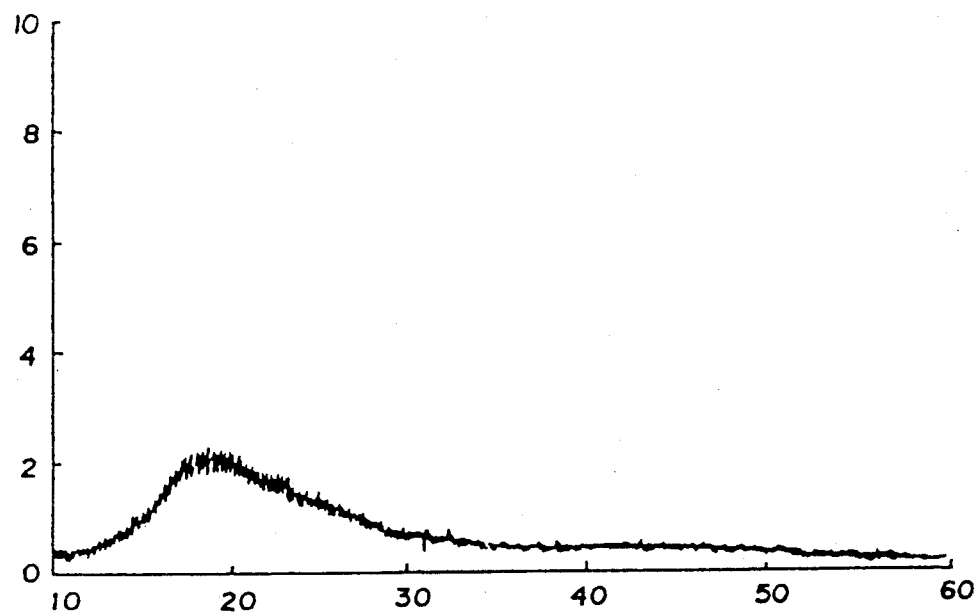
Figure 3:
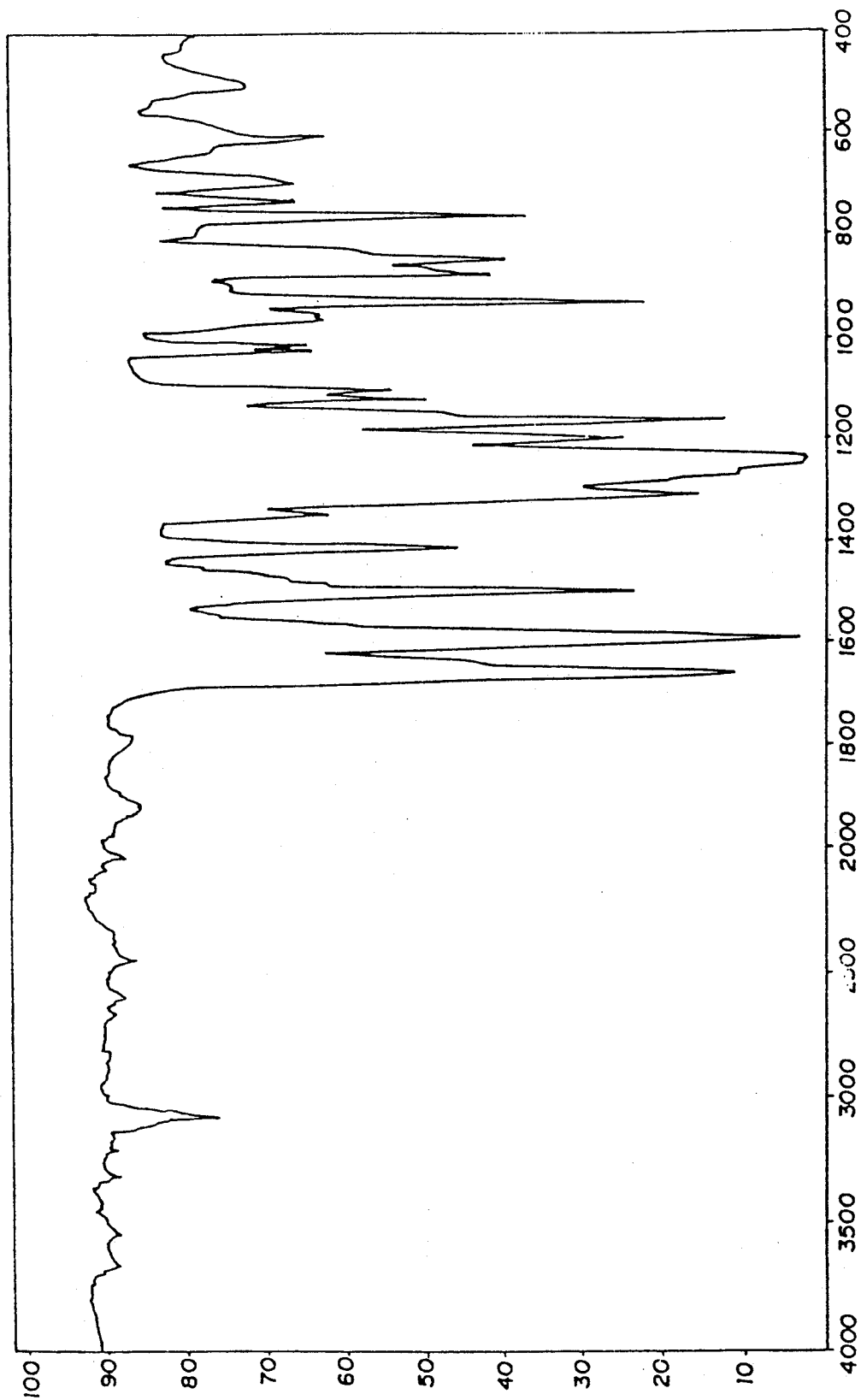

This product is soluble in chloroform, as well as in N-methylpyrrolidone. Its reduced viscosity is 0.83 dl/g as measured in the form of a 0.5% (W/V) solution in concentrated sulfuric acid at 25° C. Wide angle X ray diffraction analysis revealed that the product is amorphous. Its glass transition point measured by DSC is 207° C. FIG. 2 and FIG. 3 illustrate the wide angle X ray diffraction pattern and infrared absorption spectrum, respectively, of this copolymer. Elementary analysis data of this copolymer coincided with calculated values of a copolymer represented by the following structural formula:

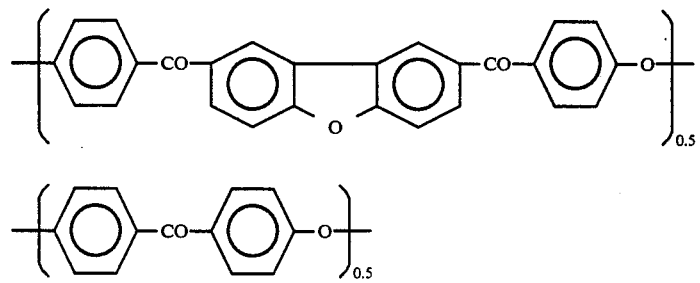

EXAMPLE 5

Into a flask having a capacity of 200 ml are charged 8.24 g (0.02 g mole) of 2,8-bis(4-fluorobenzoyl)dibenzofuran, 3.22 g (0.01 mole) of 4,4'-difluoroterephthalophenone, 4.24 g (0.04 mole) of sodium carbonate, 1.0 g of silica (Siloid 244, manufactured by Fuji-Davison Chemical Ltd.) and 20 g of diphenyl sulfone. After substituting the inner atmosphere with nitrogen, the mixture is heated from room temperature to 310° C. over about 50 minutes with stirring and reacted at that temperature for 7 hours. The reaction mixture is a viscous yellow liquid.

The reaction product is purified in the same manner as in Example 4 to obtain 10.6 g of a white-colored polymer. Wide angle X ray diffraction analysis revealed that the copolymer was amorphous. Its glass transition point is 216° C., and its reduced viscosity is 0.94 dl/g. Its elementary analysis data coincided with calculated values of a copolymer represented by the following structural formula:

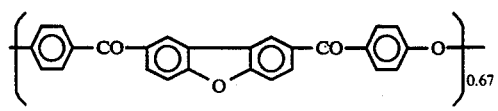

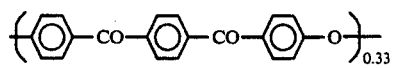

EXAMPLE 6

Into a flask having a capacity of 200 ml are charged 8.90 g (0.02 mole) of 2,8-bis(4-chlorobenzoyl)dibenzofuran, 2.51 g (0.01 mole) of 4,4'-dichlorobenzophenone, 3.71 g (0.035 mole) of sodium carbonate, 1.0 g of silica (Siloid 244, manufactured by Fuji-Davison Chemical Ltd.), 20 mg of cuprous oxide and 20 g of diphenyl sulfone. After substituting the inner atmosphere with nitrogen, the mixture is heated from room temperature to 300° C. over about 50 minutes with stirring, and reacted at that temperature for 3 hours. The reaction mixture is a viscous yellow-brown liquid.

This reaction product is purified in the same manner as in Example 4 to obtain 9.4 g of a white-colored polymer. Wide angle X ray diffraction analysis revealed that this copolymer is amorphous. Its glass transition point is 219° C., and the reduced viscosity is 0.78 dl/g. Its elementary analysis data coincided with calculated values of a copolymer represented by the following structural formula:

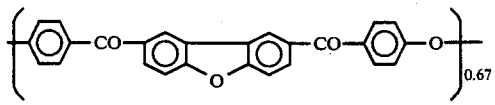

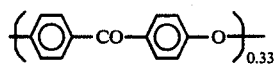

EXAMPLE 7

Into a flask having a capacity of 200 ml are charged 8.40 g (0.0204 mole) of 2,8-bis(4-fluorobenzoyl)dibenzofuran, 4.28 g (0.02 mole) of 4,4'-dihydroxybenzophenone, 2.76 g (0.02 mole) of sodium carbonate and 20 g of benzophenone. After substituting the inner atmosphere with nitrogen, the mixture is heated from room temperature to 300° C. over about 50 minutes with stirring and reacted at that temperature for 2 hours. The reaction mixture is a viscous yellow liquid.

This reaction product is purified in the same manner as in Example 4 to obtain 11.4 g of a white-colored polymer. Wide angle X ray diffraction analysis revealed that this copolymer is amorphous. Its glass transition point is 198° C., and its reduced viscosity is 0.87 dl/g. Its elementary analysis data coincided with calculated values of a copolymer represented by the following structural formula:

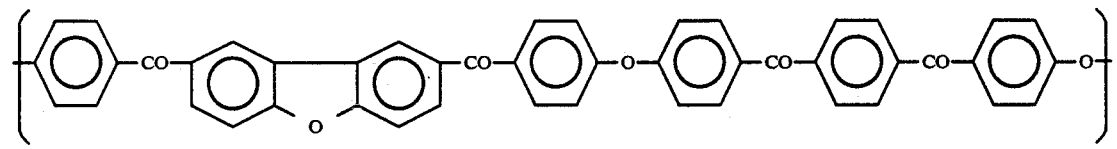

EXAMPLE 8

Into a flask having a capacity of 200 ml are charged 6.569 g (0.0204 mole) of 4,4'-difluoroterephthalophenone, 8.16 g (0.02 mole) of 2,8-bis(4-hydroxybenzoyl)-dibenzofuran, 2.76 g (0.02 mole) of potassium carbonate and 20 g of benzophenone. After substituting the inner atmosphere with nitrogen, the mixture is heated from room temperature to 300° C. in about 50 minutes with stirring and reacted at that temperature for 2 hours. The reaction mixture is a viscous yellow liquid.

This reaction product is purified in the same manner as in Example 4 to obtain 13.6 g of a white polymer. Wide angle X ray diffraction analysis revealed that this copolymer is amorphous. Its glass transition point is 202° C., and its reduced viscosity is 0.77 dl/g. Its elementary analysis data coincided with calculated values of a copolymer represented by the following structural formula:

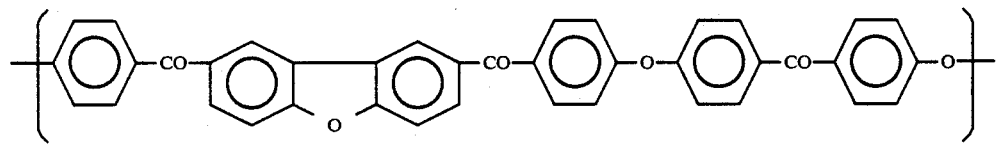

EXAMPLE 9

Into a flask having a capacity of 200 ml are charged 6.675 g (0.015 mole) of 2,8-bis(4-chlorobenzoyl)-dibenzofuran, 1.255 g (0.005 mole) of 4,4'-dichlorobenzophenone, 8.20 g (0.02 mole) of 4,4'-bis(4-hydroxybenzoyl)-diphenyl ether, 2.76 g (0.02 mole) of potassium carbonate and 25 g of diphenyl sulfone. After substituting the inner atmosphere with nitrogen, the mixture is heated from room temperature to 300° C. over about 50 minutes with stirring and reacted at that temperature for 4 hours. The reaction mixture is a viscous yellow-brown liquid.

This reaction product is purified in the same manner as in Example 4 to obtain 14.3 g of a white-colored polymer. Wide angle X ray diffraction analysis revealed that this copolymer is amorphous. Its glass transition point is 186° C., and its reduced viscosity is 0.76 dl/g. Its elementary analysis data coincided with calculated values of a copolymer represented by the following structural formula:

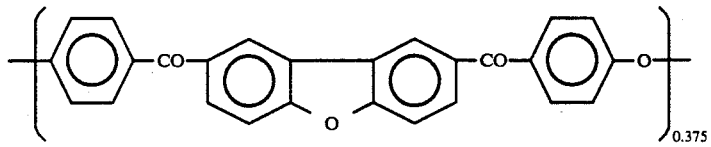

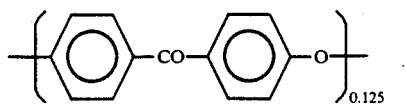

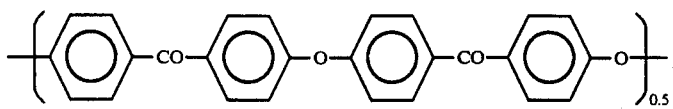

EXAMPLES 10-13

The procedure of Example 5 is repeated except that the 4,4'-difluoroterephthalophenone used in Example 5 is replaced with 0.01 mole of each of the following aromatic active dihalides. Thus, copolymers of which reduced viscosities are shown below were obtained:

| Example No. | Active dihalide | Reduced viscosity |
|---|---|---|
| 10 | 4,4'-difluoroisophthalophenone | 0.49 |
| 11 | 4,4'-bis(4-fluorobenzoyl)-diphenyl ether | 0.58 |
| 12 | 4,4'-bis(4-fluorobenzoyl)-diphenyl sulfide | 0.64 |
| 13 | 4,4'-bis(4-fluorobenzoyl)-diphenylmethane | 0.47 |

EXAMPLES 14-17

The procedure of Example 7 is repeated except that the 4,4-dihyroxybenzophenone used in Example 7 is replaced with 0.02 mole of a bisphenol or a thiophenol shown below. Thus, copolymers of which reduced viscosities are shown below were obtained.

| Example No. | Bisphenol | Reduced viscosity |
|---|---|---|
| 14 | 4,4'-bisphenol | 0.73 |
| 15 | 4,4'-dihydroxydiphenyl ether | 0.81 |
| 16 | 4,4'-dihydroxydiphenyl sulfide | 0.54 |
| 17 | 4-hydroxythiophenol | 0.77 |

INDUSTRIAL APPLICABILITY

The dibenzofuran amorphous polymer and dibenzofuran copolymer according to the present invention are excellent in heat stability, low in polarity, high in heat resistance and not low in water absorption. Accordingly, they are usable in many fields including the electrical industry.

What is claimed is:

1. A dibenzofuran amorphous polymer comprising a recurring unit represented by formula:

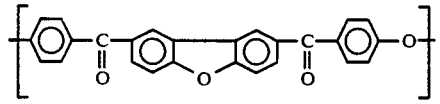

and having a molecular weight giving a reduced viscosity of at least 0.2 dl/g as measured in the form of a 0.5% (W/V) solution in N-methylpyrrolidone at 25° C.

2. A process for producing a dibenzofuran amorphous polymer comprising a recurring unit represented by formula:

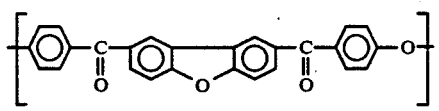

and having a molecular weight giving a reduced viscosity of at least 0.2 dl/g as measured in the form of a 0.5% (W/V) solution in N methylpyrrolidone at 25° C., which comprises reacting 2,8-bis(4-halogenobenzoyl)-dibenzofuran with a carbonate or a hydrogen carbonate of an alkali metal in the presence of a silica compound type catalyst.

3. A process for producing a dibenzofuran amorphous polymer comprising a recurring unit represented by formula:

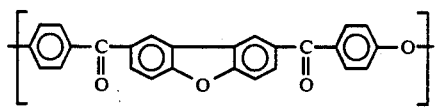

and having a molecular weight giving a reduced viscosity of at least 0.2 dl/g as measured in the form of a 0.5% (W/V) solution in N-methylpyrrolidone at 25° C., which comprises subjecting 2,8-bis(4-halogenobenzoyl)-dibenzofuran and 2,8-bis(4-hydroxybenzoyl)-dibenzofuran to a polycondensation reaction in the presence of an alkali.

4. A dibenzofuran copolymer of which molecular structure is constituted of at least one constitutional unit selected from the group consisting of constitutional unit (a) represented by formula:

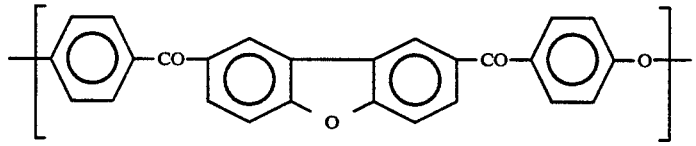

and constitutional unit (b) represented by general formula:

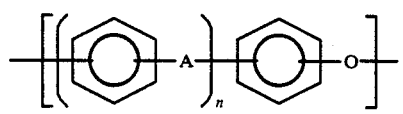

wherein A is —O—, —CO—, —S—, —SO₂O, divalent alkylene or single bond and n is a number of 0, 1, 2 or 3, the molar ratio of constitutional unit (a) to constitutional unit (b) in the copolymer molecule being in the range of 10:90 to 99:1 and said polymer having a molecular weight giving a reduced viscosity of at least 0.2 dl/g as measured in the form of a 0.5% (W/V) solution in concentrated sulfuric acid at 25° C.

5. A process for producing a dibenzofuran copolymer of which molecular structure is constituted of at least one constitutional unit selected from the group consisting of constitutional unit (a) represented by formula:

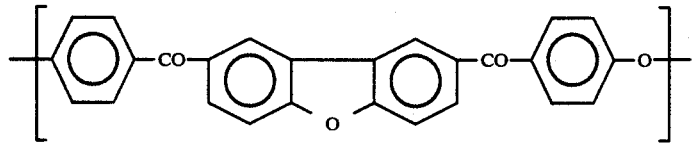

and constitutional unit (b) represented by general formula:

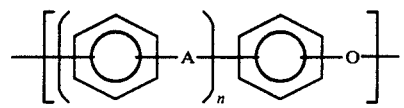

wherein A and n are the same as defined above, the molar ratio of constitutional unit (a) to constitutional unit (b) in the copolymer molecule being in the range of 10:90 to 99:1 and said polymer having a molecular weight giving a reduced viscosity of at least 0.2 dl/g as measured in the form of a 0.5% (W/V) solution in concentrated sulfuric acid at 25° C., which comprises reacting a carbonate or a hydrogen carbonate of an alkali metal with 2,8-bis(4-halogenobenzoyl)-dibenzofuran and an aromatic dihalide represented by the following formula:

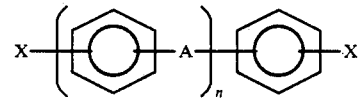

wherein X is halogen and A and n are the same as defined above, in the presence of a silica compound type catalyst.

6. A process for producing a dibenzofuran copolymer of which molecular structure is constituted of at least one constitutional unit selected from the group consisting of constitutional unit (a) represented by formula:

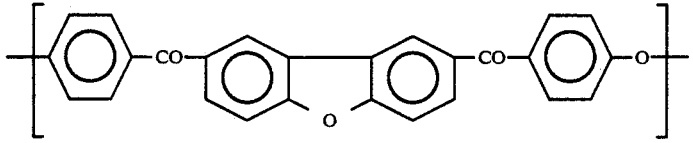

and constitutional unit (b) represented by the following general formula:

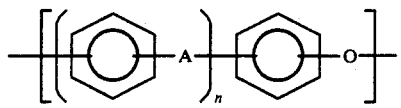

wherein A and n are the same as defined above, the molar ratio of constitutional unit (a) to constitutional unit (b) in the copolymer molecule being in the range of 10:90 to 99:1 and said polymer having a molecular weight giving a reduced viscosity of at least 0.2 dl/g as measured in the form of a 0.5% (W/V) solution in concentrated sulfuric acid at 25° C., which comprises subjecting:

(i) 2,8-bis(4-halogenobenzoyl)-dibenzofuran or a mixture of 2,8-bis(4-halogenobenzoyl)-dibenzofuran with at least one aromatic dihalide represented by the following general formula:

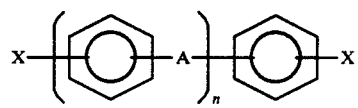

wherein X is a halogen, and A and n are the same as defined above; and (ii) 2,8-bis(4-hydroxybenzoyl)-dibenzofuran or a mixture of 2,8-bis(4-hydroxybenzoyl)-dibenzofuran with at least one aromatic dihydroxy compound represented by the following general formula:

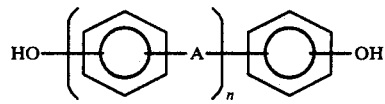

wherein A and n are the same as defined above, to a polycondensation reaction in the presence of an alkali.

7. A dibenzofuran polymer selected from the group consisting of
(a) a dibenzofuran amorphous polymer comprising a recurring unit represented by formula:

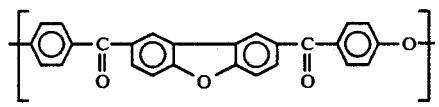

and having a molecular weight giving a reduced viscosity of at least 0.2 dl/g as measured in the form of a 0.5% (W/V) solution in N-methylpyrrolidone at 25° C. and (b) a dibenzofuran copolymer of which molecular structure is constituted of at least one constitutional unit selected from the group consisting of constitutional unit (a) represented by formula:

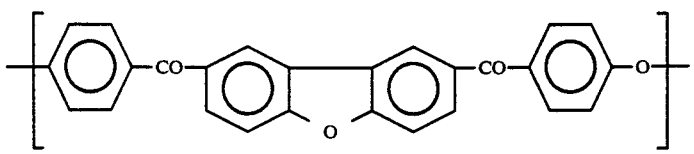

and constitutional unit (b) represented by general formula:

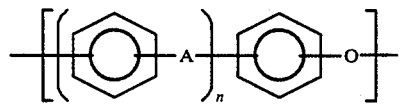

wherein A is —O—, —CO—, —S—, —SO$_2$O, divalent alkylene or single bond and n is a number of 0, 1, 2 or 3, the molar ratio of constitutional unit (a) to constitutional unit (b) in the copolymer molecule being in the range of 10:90 to 99:1 and said polymer having a molecular weight giving a reduced viscosity of at least 0.2 dl/g as measured in the form of a 0.5% (W/V) solution in concentrated sulfuric acid at 25° C.

8. A process for producing a dibenzofuran polymer selected from the group consisting of (a) a dibenzofuran amorphous polymer comprising a recurring unit represented by formula:

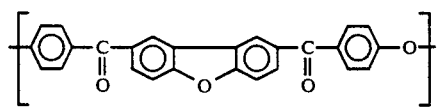

and having a molecular weight giving a reduced viscosity of at least 0.2 dl/g as measured in the form of a 0.5% (W/V) solution in N-methylpyrrolidone at 25° C. and (b) a dibenzofuran copolymer of which molecular structure is constituted of at least one constitutional unit selected from the group consisting of constitutional unit (a) represented by formula:

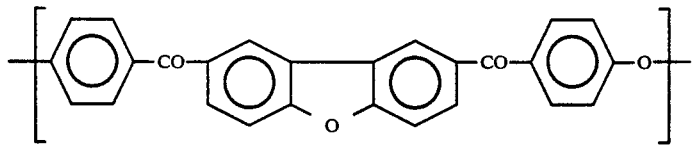

and constitutional unit (b) represented by general formula:

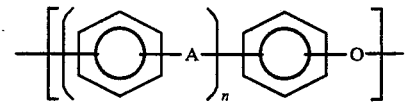

wherein A is —O—, —CO—, —S—, —SO$_2$O, divalent alkylene or single bond and n is a number of 0, 1, 2 or 3, the molar ratio of constitutional unit (a) to constitutional unit (b) in the copolymer molecular being in the range of 10:90 to 99:1 and said polymer having a molecular weight giving a reduced viscosity of at least 0.2 dl/g as measured in the form of a 0.5% (W/V) solution in concentrated sulfuric acid at 25° C., wherein the dibenzofuran amorphous polymer (a) is produced by reacting 2,8-bis(4-halogenobenzoyl)-dibenzofuran with a carbonate or a hydrogen carbonate of an alkali metal in the presence of a silica compound type catalyst or by subjecting 2,8-bis(4-halogenobenzoyl)-dibenzofuran and 2,8-bis(4-hydroxybenzoyl)-dibenzofuran to a polycondensation reaction in the presence of an alkali, and wherein the dibenzofuran copolymer (b) is produced by reacting a carbonate or a hydrogen carbonate of an alkali metal with 2,8-bis(4-halogenobenzoyl)-dibenzofuran and an aromatic dihalide represented by the following formula:

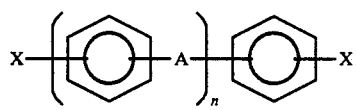

wherein X is halogen and A and n are the same as defined above, in the presence of a silica compound type catalyst and wherein the dibenzofuran copolymer (b) is produced by subjecting:
(i) 2,8-bis(4-halogenobenzoyl)-dibenzofuran or a mixture of 2,8-bis(4-halogenobenzoyl)-dibenzofuran with at least one aromatic dihalide represented by the following general formula:

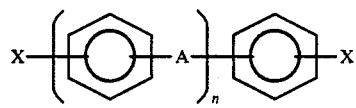

wherein X is a halogen, and A and n are the same as defined above; and
(ii) 2,8-bis(4-hydroxybenzoyl)-dibenzofuran or a mixture of 2,8-bis(4-hydroxybenzoyl)-dibenzofuran with at least one aromatic dihydroxy compound represented by the following general formula:

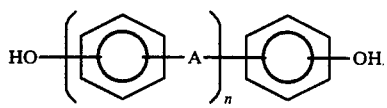

wherein A and n are the same as defined above, to a polycondensation reaction in the presence of an alkali.

9. The benzofuran polymer of claim 7, wherein the group selected is the dibenzofuran copolymer (b) in which said constitutional unit (a) occupies at least 70% by mole of the total dibenzofuran structure.

10. The process of claim 8, wherein the dibenzofuran copolymer (b) in which said constitutional unit (a) occupies at least 70% by mole of the total dibenzofuran structure.

* * * * *